United States Patent
Harris et al.

(10) Patent No.: US 7,524,988 B2
(45) Date of Patent: *Apr. 28, 2009

(54) PREPARATION OF ACETIC ACID

(75) Inventors: Stephen H. Harris, Kennett Square, PA (US); Brian A. Salisbury, Oxford, PA (US); Ronnie M. Hanes, Crofton, MD (US)

(73) Assignees: Lyondell Chemical Technology, L.P., Greenville, DE (US); Millennium Petrochemicals Inc., Houston, TX (US)

( * ) Notice: Subject to any disclaimer, the term of this patent is extended or adjusted under 35 U.S.C. 154(b) by 232 days.

This patent is subject to a terminal disclaimer.

(21) Appl. No.: 11/496,900

(22) Filed: Aug. 1, 2006

(65) Prior Publication Data

US 2008/0033206 A1    Feb. 7, 2008

(51) Int. Cl.
    *C07C 51/42*    (2006.01)
(52) U.S. Cl. .................................................... 562/608
(58) Field of Classification Search .................. 562/608
    See application file for complete search history.

(56) References Cited

U.S. PATENT DOCUMENTS

| | | | |
|---|---|---|---|
| 3,769,329 A | 10/1973 | Paulik et al. ............ | 260/488 K |
| 5,155,265 A | 10/1992 | Scates et al. ................ | 562/608 |
| 5,155,266 A | 10/1992 | Scates et al. ................ | 562/608 |
| 5,202,481 A | 4/1993 | Scates et al. ................ | 562/608 |
| 5,371,286 A | 12/1994 | Blay et al. .................. | 562/519 |
| 5,387,713 A | 2/1995 | Cook et al. .................. | 562/608 |
| 5,620,567 A | 4/1997 | Seidel et al. .................. | 203/24 |
| 5,625,095 A | 4/1997 | Miura et al. ................ | 562/519 |
| 5,783,731 A | 7/1998 | Fisher et al. ................ | 562/519 |
| 5,817,869 A | 10/1998 | Hinnenkamp et al. ....... | 562/519 |
| 5,932,764 A | 8/1999 | Morris et al. ............... | 562/519 |
| 6,143,930 A | 11/2000 | Singh et al. ................ | 562/608 |
| 6,232,491 B1 | 5/2001 | Cunnington et al. ........ | 560/248 |
| 6,323,364 B1 | 11/2001 | Agrawal et al. ............. | 562/519 |
| 6,339,171 B1 | 1/2002 | Singh et al. ................ | 562/519 |
| 6,416,237 B2 | 7/2002 | Lissotschenko et al. ....... | 385/88 |
| 6,667,418 B2 | 12/2003 | Broussard et al. ........... | 562/519 |

FOREIGN PATENT DOCUMENTS

| | | |
|---|---|---|
| EP | 0487284 A2 | 5/1992 |
| EP | 0638538 A1 | 2/1995 |
| WO | PCT/US2007/016563 | 1/2008 |

*Primary Examiner*—Taylor Victor Oh
(74) *Attorney, Agent, or Firm*—Shao-Hua Guo

(57) ABSTRACT

A method for removing aldehyde impurities from an acetic acid stream is disclosed. The method comprises reacting an acetic acid stream containing aldehyde impurities with a hydroxyl compound to form corresponding acetals. The acetals are subsequently removed from the acetic acid by, e.g., distillation.

15 Claims, No Drawings

PREPARATION OF ACETIC ACID

FIELD OF THE INVENTION

The invention relates to preparation of acetic acid. More particularly, the invention relates to a method for removing aldehyde impurities from acetic acid.

BACKGROUND OF THE INVENTION

The carbonylation of methanol produces acetic acid:

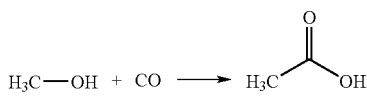

Prior to 1970, acetic acid was made using cobalt catalysts. A rhodium carbonyl iodide catalyst was developed in 1970 by Monsanto. The rhodium catalyst is considerably more active than the cobalt catalyst, which allows lower reaction pressure and temperature. Most importantly, the rhodium catalyst gives high selectivity to acetic acid.

One problem with the original Monsanto process is that a large amount of water (about 14%) is needed to produce hydrogen in the reactor via the water-gas shift reaction (CO+ $H_2O=CO_2+H_2$). Water and hydrogen are needed to react with precipitated Rh(III) and inactive $[RhI_4(CO)_2]^-$ to regenerate the active Rh(I) catalyst. The large amount of water increases the amount of hydrogen iodide, which is highly corrosive and leads to engineering problems. Further, removing a large amount of water from the acetic acid product is costly.

In the late '70s, Celanese modified the Monsanto process by adding lithium iodide salt to the carbonylation. Lithium iodide salt increases the catalyst stability by minimizing the side reactions that produce inactive Rh(III) species and therefore the amount of water needed is reduced. However, the high concentration of lithium iodide salt promotes stress crack corrosion of the reactor vessels. Furthermore, the use of iodide salts increases the iodide impurities in the acetic acid product.

In the late '90s, Lyondell Chemical Company (by its predecessors) developed a new rhodium carbonylation catalyst system that does not use iodide salt. The catalyst system uses a pentavalent Group VA oxide such as triphenylphosphine oxide as a catalyst stabilizer. The Lyondell catalyst system not only reduces the amount of water needed but also increases the carbonylation rate and acetic acid yield. See U.S. Pat. No. 5,817,869.

One challenge still facing the industry is that lowering water concentration in the methanol carbonylation results in increased aldehyde formation. Methods for reducing aldehyde concentration in acetic acid are known. For instance, U.S. Pat. No. 6,667,418 discloses a method for reducing aldehydes by oxidizing them with air, hydrogen peroxide, and other free radical initiators in an integrated acetic acid production process at an elevated temperature. Introducing free radical initiators into acetic acid production process is inconvenient because free radical initiators are explosive.

New method for reducing aldehydes in acetic acid is needed. Ideally, the method could be performed conveniently and safely.

SUMMARY OF THE INVENTION

The invention is a method for the preparation of acetic acid. The method comprises reacting an acetic acid stream containing an aldehyde impurity with a hydroxyl compound to convert the aldehyde impurity to an acetal. The acetal is then separated from the acetic acid by, e.g., distillation.

DETAILED DESCRIPTION OF THE INVENTION

An acetic acid stream containing aldehyde impurities is produced by methanol carbonylation. Examples of aldehyde impurities include acetaldehyde, crotonaldehyde, butyraldehyde, their derivatives such as 2-ethyl crotonaldehyde, 2-ethyl butyraldehyde, the like, and mixtures thereof. The method of the invention is preferably used to remove light aldehyde impurities. By "light," we mean any aldehyde impurity that has a relatively low boiling point compared to acetic acid. Examples of light aldehyde impurities include acetaldehyde and butyraldehyde.

The carbonylation reaction is usually performed in the presence of a carbonylation catalyst and a catalyst stabilizer. Suitable carbonylation catalysts include those known in the acetic acid industry. Examples of suitable carbonylation catalysts include rhodium catalysts and iridium catalysts.

Suitable rhodium catalysts are taught, for example, by U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_2$, the like, and mixtures thereof.

Suitable iridium catalysts are taught, for example, by U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2 I]_2$, $[Ir(CO)_2Cl]_2$, $[Ir(CO)_2Br]_2$, $[Ir(CO)_4I_2]^-H^+$, $[Ir(CO)_2]^-H^+$, $[Ir(CO)_2I_2]^-H^+$, $[Ir(CH_3)I_3(CO)_2]^-H^+$, $Ir_4(CO)_{12}$, $IrCl_3 \cdot 4H_2O$, $IrBr_3 \cdot 4H_2O$, $Ir_3(CO)_{12}$, $Ir_2O_3$, $IrO_2$, $Ir(acac)(CO)_2$, $Ir(acac)_3$, $Ir(Ac)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates.

The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are chloride-free such as acetates.

Preferably, the reaction is performed in the presence of a catalyst stabilizer. Suitable catalyst stabilizers include those known to the industry. In general, there are two types of catalyst stabilizers. The first type of catalyst stabilizer is metal iodide salt such as lithium iodide. The second type of catalyst stabilizer is a non-salt stabilizer. Preferred non-salt stabilizers are pentavalent Group VA oxides. See U.S. Pat. No. 5,817, 869. Phosphine oxides are more preferred. Triphenylphosphine oxides are most preferred.

The carbonylation reaction is performed in the presence of water. Preferably, the concentration of water present is from about 2 wt % to about 14 wt % based on the total weight of the reaction medium. More preferably, the water concentration is from about 2 wt % to about 10 wt %. Most preferably, the water concentration is from about 4 wt % to about 8 wt %.

The reaction is performed in the presence of methyl acetate. Methyl acetate can be formed in situ. If desirable, methyl acetate can be added as a starting material to the reaction mixture. Preferably, the concentration of methyl acetate is from about 2 wt % to about 20 wt % based on the total weight of the reaction medium. More preferably, the concentration of methyl acetate is from about 2 wt % to about 16 wt %. Most preferably, the concentration of methyl acetate is from about 2 wt % to about 8 wt %. Alternatively, methyl acetate or a mixture of methyl acetate and methanol from byproduct streams of the hydroysis/methanolysis of polyvinyl acetate can be used for the carbonylation reaction.

Preferably, the reaction is performed in the presence of methyl iodide. Methyl iodide is a catalyst promoter. Preferably, the concentration of methyl iodide is from about 0.6 wt % to about 36 wt % based on the total weight of the reaction medium. More preferably, the concentration of methyl iodide is from about 4 wt % to about 24 wt %. Most preferably, the concentration of methyl iodide is from about 6 wt % to about 20 wt %. Alternatively, methyl iodide can be generated in the carbonylation reactor by adding hydrogen iodide (HI).

Hydrogen may also be fed into the reactor. Addition of hydrogen can enhance the carbonylation efficiency. Preferably, the concentration of hydrogen is from about 0.1 mol % to about 5 mol % of carbon monoxide in the reactor. More preferably, the concentration of hydrogen is from about 0.3 mol % to about 3 mol % of carbon monoxide in the reactor.

Methanol and carbon monoxide are fed to the carbonylation reactor. The methanol feed to the carbonylation reaction can come from a syngas-methanol facility or any other source. Methanol does not react directly with carbon monoxide to form acetic acid. It is converted to methyl iodide by the hydrogen iodide present in the acetic reactor and then reacts with carbon monoxide and water to give acetic acid and regenerate the hydrogen iodide. Carbon monoxide not only becomes part of the acetic acid molecule, but it also plays an important role in the formation and stability of the active catalyst.

The carbonylation reaction is preferably performed at a temperature within the range of about 150° C. to about 250° C. More preferably, the reaction is performed at a temperature within the range of about 150° C. to about 200° C. The carbonylation reaction is preferably performed under a pressure within the range of about 200 psig to about 2,000 psig. More preferably, the reaction is performed under a pressure within the range of about 300 psig to about 500 psig.

An acetic acid product stream is usually withdrawn from the reactor and is separated, by a flash separation, into a liquid fraction comprising the catalyst and the catalyst stabilizer and a vapor fraction comprising the acetic acid product, the reactants, water, methyl iodide, and impurities generated during the carbonylation reaction including aldehydes. The liquid fraction is then recycled to the carbonylation reactor. The vapor fraction is then passed to a distillation column.

The distillation column, the so called "light ends distillation," separates an overhead comprising methyl iodide, water, methanol, methyl acetate, and impurities including aldehyde impurities from an acetic acid stream comprising acetic acid, a small amount of water, and heavy impurities. The acetic acid stream may be passed to a drying column to remove water and then be subjected to distillation, so called "heavy ends distillation," to remove the heavy impurities such as propionic acid.

The overhead from the light ends distillation preferably comprises from about 60 wt % to about 90 wt % of methyl iodide, from about 5 wt % to about 15 wt % of methyl acetate, from about 1 wt % to about 10 wt % of acetic acid, 1 wt % or less of water, from about 1 wt % to about 10 wt % of alkane impurities, and about 2 wt % or less of aldehyde impurities based on the total weight of the overhead.

The overhead is condensed and separated in a decanter to a light, aqueous phase and a heavy, organic phase. The heavy, organic phase comprises methyl iodide and the aldehyde impurity. The light, aqueous phase comprises water, acetic acid, and methyl acetate. The aqueous phase is usually recycled to the reactor or to the light ends distillation.

According to the method of the invention, at least a portion of the heavy, organic phase is treated with a hydroxyl compound to convert the aldehydes to acetals. Preferably, about 5% to about 50% of the heavy, organic phase is treated with a hydroxyl compound. More preferably, about 5% to about 25% of the heavy, organic phase is treated with a hydroxyl compound. The treated, heavy, organic phase is then directed to the light ends distillation column. Due to their high boiling points, the acetals go with the acetic acid product stream as heavy impurities and are subsequently removed from the acetic acid product by the heavy ends distillation.

Alternatively, the treated heavy, organic phase is separated by a distillation column into a fraction, which comprises a majority of the acetal for disposal, and a fraction that comprises a majority of methyl iodide, which is recycled back to the decanter heavy phase or to the carbonylation reaction. By "majority", we mean that the concentration of the relevant component is greater than 50% of the total weight of the fraction.

Suitable hydroxyl compounds for reacting with the aldehydes include alcohols, glycols, and polyols. Suitable alcohols include $C_4$ to $C_{10}$ alcohols. Sterically bulky alcohols, such as 2-ethylhexan-1-ol, 2-methylhexan-2-ol, 3-methylpentan-3-ol, 2-methylpentan-2-ol, 3-methyl-2-butanol, 2-methylbutan-2-ol, and 3-methyl-2-butanol, are preferred. By "glycol," we mean any compound that has two hydroxyl groups. Suitable glycols include ethylene glycol, propylene glycol, 1,4-butanediol, 1,3-butanediol, 1,5-pentanediol, 1,6-hexanediol, 2-methyl-1,3-propanediol, 2,2-dimethyl-1,3-propanediol, cyclohexane-1,4-dimethanol, and neopentyl glycol, the like, and mixtures thereof. Suitable polyols include those which have three or more hydroxyl functional groups such as glycerin. Glycols are preferred because they form stable cyclic acetals with aldehydes. Ethylene glycol is most preferred because it is inexpensive and readily available.

Preferably, the treatment with hydroxyl compounds is performed at a temperature within the range of about 20° C. to about 135° C. More preferably, the temperature is within the range of about 20° C. to about 50° C. Preferably, the treatment is performed in the presence of an acid catalyst. More preferably, the acid catalyst is an ion exchange resin.

Preferably, the hydroxyl compound is used in an amount within the range of about 1 equivalent to about 10 equivalents of the aldehyde impurities. More preferably, the hydroxyl compound is used in an amount within the range of about 2 equivalents to about 5 equivalents of the aldehyde impurities.

The following examples merely illustrate the invention. Those skilled in the art will recognize many variations that are within the spirit of the invention and scope of the claims.

EXAMPLE 1

A decanter heavy phase type solution (25 g), which contains 79 wt % methyl iodide, 4.8 wt % of acetic acid, 9.5 wt % of methyl acetate, 5.7 wt % of isooctane, 500 ppm of water, and 500 ppm of acetaldehyde, is placed into a round bottomed flask. Amberlyst®15 (an acidic ion exchange resin, 0.5 g, product of Sigma-Aldrich) is added to the reactor and the mixture is stirred. Ethylene glycol (630 mL, 2 equivalents of acetaldehyde) is added via syringe to the mixture and the reaction continues for 30 minutes. The GC analysis indicates that 93% of the acetaldehyde is converted to acetal.

EXAMPLE 2

An ATR (attenuated total reflectance) infrared probe, coupled via optic conduit to an infrared spectrometer, is inserted into one neck of a two-necked, round-bottomed flask. Amberlyst 15 (1.1 g) is added to the flask followed by 5 mL of a solution having 3.8 wt % of acetaldehyde, 7.3 wt % of ethylene glycol (1.3 equivalence based on acetaldehyde), and 88.9 wt % of methyl iodide. The resultant slurry contains about 0.4 g of acetaldehyde per g of Amberlyst 15. Infrared spectra are obtained on a periodic basis for a total period of about 15 minutes at room temperature. The decrease in absorption of an infrared signal of acetaldehyde at $1724\ cm^{-1}$ and the corresponding increase in absorption of an infrared signal of the corresponding cyclic acetal at $1140\ cm^{-1}$ are both monitored. Analysis of the spectra shows that about 80% of the acetaldehyde is converted to the acetal after 1 minute of reaction.

EXAMPLE 3

The general procedure of Example 2 is repeated but 1,3-propanediol, 1,3-butanediol, and 1,4-butanediol, rather than ethylene glycol, are respectively used. After 1 minute of reaction, the aldehyde conversion is about 42% for 1,3-propanediol, 52% for 1,3-butanediol, and 69% for 1,4-butanediol.

EXAMPLE 4

The general procedure of Example 2 is repeated but the solution contains 3.2 wt % of acetic acid, 8.2 wt % of methyl acetate, 6.4 wt % of 3-methylpentane, 70.8 wt % of methyl iodide, 4.2 wt % of acetaldehyde, and 7.2 wt % of ethylene glycol and it is mixed with variable amounts of Amberlyst 15 resin to obtain 0.4 g, 0.7 g, and 1.2 g of acetaldehyde per g of Amberlyst 15 resin respectively. The reactions are monitored by the inserted infrared probe. The results show that after 1 minute of reaction, the aldehyde conversions are about 71%, 50%, and 15%.

EXAMPLE 5

The general procedure of Example 4 is repeated with hydriodic acid rather than Amberlyst 15. Five mL of a solution as described in Example 4 is added to a round-bottomed flask, followed by 0.34 g of 57% aqueous hydriodic acid solution. The concentration of hydriodic acid in the resulting solution is 1.9 wt %. Analysis of the solution via infrared probe shows immediate conversion of about 65% of acetaldehyde to the corresponding acetal.

EXAMPLE 6

In each case involving a set of four experiments, A-D, a glass column of 8 mm internal diameter is loaded with 1.15 g (1.8 mL) of Amberlyst 15 resin. This volume of resin is referred to as the bed volume (BV). The length to diameter ratio (l/d) of this resin bed is approximately 2.5. Decanter heavy phase type solutions of composition shown in Table 1 are used as feed for these columns. Glycol or polyol is present in molar equivalency relative to acetaldehyde. The decanter heavy phase type solutions are gravity fed through a water-cooled condenser to the top of the column. The purpose of the condenser is to prevent evaporation of the low boiling point acetaldehyde prior to its reaction in the column. The column itself is maintained at room temperature. Flow rate through the column is adjusted via manipulation of a take-off valve. Aliquots of column eluate are collected into chilled vials and subsequently analyzed by infrared probe to determine the extent of acetaldehyde conversion to appropriate acetal.

The results show that the acetaldehyde reaction rate is sufficiently rapid such that conversions of 75%-95% (depending on glycol/polyol) can be achieved at a flow rate of about 50 BV/hr. In fact, even at flow rates as high as 100 BV/hr, conversion percentages drop only slightly to a range of 60%-95% (depending on glycol/polyol).

We claim:

1. A method for reducing an aldehyde impurity from acetic acid stream, said method comprising:
   (a) reacting methanol and carbon monoxide in the presence of a carbonylation catalyst, a catalyst stabilizer, methyl iodide, water and methyl acetate to produce an acetic acid stream comprising the catalyst, the catalyst stabilizer, methyl iodide, methyl acetate, water, acetic acid, and an aldehyde impurity;
   (b) flashing at least a portion of the acetic acid stream to a vapor stream comprising acetic acid, water, methyl acetate, methyl iodide and the aldehyde impurity, and a liquid stream comprising the catalyst and the catalyst stabilizer;
   (c) recycling the liquid stream to the reaction of step (a);
   (d) separating the vapor stream by distillation into an acetic acid product stream comprising acetic acid and water, and an overhead stream comprising methyl iodide, water, methyl acetate, acetic acid, and the aldehyde impurity;
   (e) condensing the overhead stream to produce a light, aqueous phase comprising water, acetic acid, and methyl acetate, and a heavy, organic phase comprising methyl iodide and the aldehyde impurity;
   (f) reacting at least a portion of the heavy, organic phase with a hydroxyl compound selected from the group consisting of $C_{4-10}$ alcohols, glycols, and glycerin to convert the aldehyde impurity to an acetal having a higher boiling point than acetic acid;
   (g) recycling the treated heavy phase of step (f) to the distillation of step (d), wherein the acetal goes with the acetic acid product stream as a heavy impurity; and
   (h) separating the acetal from the acetic acid product stream of step (g) by distillation.

2. The method of claim 1, wherein the catalyst is a rhodium catalyst.

3. The method of claim 1, wherein the catalyst stabilizer is selected from the group consisting of pentavalent Group VA oxides, metal iodide salts, and mixtures thereof.

4. The method of claim 1, wherein the catalyst stabilizer is a phosphine oxide.

5. The method of claim 1, wherein the catalyst stabilizer is triphenylphosphine oxide.

6. The method of claim 1, wherein the water concentration of step (a) is 10 wt % or less based on the total acetic acid stream.

7. The method of claim 1, wherein the water concentration of step (a) is 6 wt % or less based on the total weight of the acetic acid stream.

8. The method of claim 1, wherein the aldehyde impurity is acetaldehyde.

9. The method of claim 1, wherein the hydroxyl compound is a glycol selected from the group consisting of ethylene glycol, propylene glycol, 1,4-butanediol, 1,3-butanediol, 1,5-pentanediol, 1,6-hexanediol, 2-methyl-1,3-propanediol, 2,2-dimethyl-1,3-propanediol, cyclohexane-1,4-dimethanol, neopentyl glycol, and mixtures thereof.

10. The method of claim 1, wherein the hydroxyl compound is ethylene glycol.

11. The method of claim 1, wherein the reaction of step (f) is performed in the presence of an acid catalyst.

12. The method of claim 11, wherein the catalyst is an acidic ion exchange resin.

13. The method of claim 1, where the reaction of step (f) is performed at a temperature within the range of about 20° C. to about 135° C.

14. The method of claim 1, wherein the reaction of step (f) is performed at a temperature within the range of about 20° C. to about 50° C.

15. The method of claim 1, wherein the heavy phase of step (e) comprises from 60 wt % to 90 wt % of methyl iodide, 1 wt % to 10 wt % of acetic acid, 5 wt % to 15 wt % of methyl acetate, 1 wt % to 10 wt % of an alkane, 1 wt % or less of water, and 2 wt % or less of the aldehyde impurity.

* * * * *